(12) United States Patent
Myerson et al.

(10) Patent No.: US 7,931,680 B2
(45) Date of Patent: Apr. 26, 2011

(54) PLATE FOR LENGTHENING THE LATERAL COLUMN OF THE FOOT

(75) Inventors: Mark Myerson, Baltimore, MD (US); Priya Prasad, Warsaw, IN (US); Chris Bremer, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 95 days.

(21) Appl. No.: 11/094,993

(22) Filed: Mar. 31, 2005

(65) Prior Publication Data
US 2006/0241609 A1    Oct. 26, 2006

(51) Int. Cl.
*A61B 17/88* (2006.01)
(52) U.S. Cl. .......................................... 606/281
(58) Field of Classification Search ............... 606/69, 606/70, 71
See application file for complete search history.

(56) References Cited

U.S. PATENT DOCUMENTS

| | | | | |
|---|---|---|---|---|
| 1,105,105 A * | 7/1914 | Sherman | | 606/286 |
| 4,628,936 A | 12/1986 | Langer et al. | | |
| 6,008,433 A * | 12/1999 | Stone | | 623/20.14 |
| 6,235,032 B1 | 5/2001 | Link | | |
| 6,514,274 B1 * | 2/2003 | Boucher et al. | | 606/232 |
| 6,565,570 B2 * | 5/2003 | Sterett et al. | | 606/69 |
| 2002/0128654 A1 * | 9/2002 | Steger et al. | | 606/69 |
| 2003/0199875 A1 * | 10/2003 | Mingozzi et al. | | 606/69 |
| 2004/0093081 A1 | 5/2004 | Nilsson et al. | | |
| 2004/0127902 A1 * | 7/2004 | Suzuki et al. | | 606/69 |
| 2005/0075641 A1 * | 4/2005 | Singhatat et al. | | 606/86 |
| 2005/0171539 A1 * | 8/2005 | Braun et al. | | 606/61 |
| 2006/0036250 A1 * | 2/2006 | Lange et al. | | 606/69 |

FOREIGN PATENT DOCUMENTS
FR    2764183        12/1998
FR    2764183 A1  *  12/1998

OTHER PUBLICATIONS

Hockenbury, Todd R., "Acquired Flatfoot," http://www.emedicine.com/orthoped/topic461.html, Mar. 7, 2005, 20 pages.
"Flat Foot Implant," Kalix®, Intergra™, unknown date, 3 pages.
Galluzzo, A.J., "Galluzzo Foot & Ankle Clinic," http://www.footdoc-il.com/coupon.htm, Mar. 7, 2005, 10 pages.

* cited by examiner

*Primary Examiner* — Thomas C Barrett
*Assistant Examiner* — Nicholas Woodall
(74) *Attorney, Agent, or Firm* — Maginot, Moore & Beck

(57) ABSTRACT

An implant for lengthening the lateral column of the foot is configured for engagement across the calcaneocuboid joint or across a space formed between two bone segments of the calcaneus bone. The implant includes a plate configured positioning on the bone segments and includes an array of screw holes at its opposite ends arranged for solid fixation to the corresponding bone using bone screws. The implant includes a wedge projecting from the bone engaging surface of the plate. The wedge has a width that is tapered toward the plantar aspect and toward the medial aspect of the foot.

10 Claims, 2 Drawing Sheets

PLATE FOR LENGTHENING THE LATERAL COLUMN OF THE FOOT

BACKGROUND OF THE INVENTION

The present invention relates to implants for the correction of anatomic segments of the human foot. In particular, the invention provides means for lengthening the lateral column of the foot.

The foot is a complex structure of skeletal components and ligaments that interact to produce walking, running and jumping motions, and that act as a shock absorber during these motions. The foot often absorbs up to 2½ times the body weight in load. Subtalar joint pronation is a complex motion that is typically invoked during a heel strike. Pronation effectively "unlocks" the bones of the foot to render it loose and mobile so that the foot can effectively adapt to the supporting surface. Proper pronation facilitates flexion of the knee during walking and running.

On the other hand, supination is essentially the opposite of pronation and is a motion that effectively "locks" the bones of the foot to convert the foot into a more rigid lever in preparation for the transfer of body weight forward to the toes. Proper supination facilitates proper extension of the knee during movement, and is therefore a necessary motion to permit a gait that is both efficient and low in impact shock.

Abnormal supination or pronation typically results in problems within the foot, ankle, knee and even the hip. For instance, hyperpronation, or flatfoot syndrome, has been found in 95% of the patients with total knee replacements. Acquired adult flatfoot arises from numerous causes, including fracture or dislocation, tendon laceration, tarsal coalition, arthritis, neuroarthropathy, neurologic weakness and iatrogenic causes. The most common cause of acquired flatfoot is posterior tibial tendon dysfunction.

Conservative treatment regimes include the use of orthotics to mechanically introduce proper pronation or supination, stretching exercises where the abnormality is due to ligament tension, and medication for pain relief. These conservative approaches may provide enough relief for the patient to assume a near normal gait and level of physical activity, but will not provide any significant correction at the point of contact.

In many cases, surgical correction is necessary to address problems with improper or excessive supination or pronation. For instance, surgical treatments for flatfoot includes tenosynovectomy, osteotomy of the heel bone (calcaneous), tendon transfer, arthrodesis (fusion of adjacent bones), and lateral column lengthening. Of these procedures, the latter is often preferred because it helps realign the bones of the foot and restores a proper arch in the foot.

The Evan anterior calcaneal lengthening osteotomy is one surgical procedure that lengthens the lateral column of the foot by inserting a 10-15 mm bone graft 10-15 mm proximal to the calcaneocuboid joint. This procedure improves forefoot abduction and hind foot valgus, and restores midfoot arch. This procedure is often performed in conjunction with posterior tibial tendon repair or shortening, and deltoid ligament repair or reconstruction as indicated.

In another approach, lateral column lengthening is accomplished through distraction arthrodesis of the calcaneocuboid joint. The procedure is usually accompanied by FDL (flexor digitorum longus) or FHL (flexor hallucis longus) transfer and selective midfoot arthrodesis. In one typical procedure, a 5 cm dorsolateral incision is made over the calcaneocuboid joint and the sural nerve and peroneal tendons are retracted plantarly. The joint is exposed and the articular cartilage removed with osteotomes and curettes. The joint is then distracted using a smooth laminar spreader. Alternatively, a small external fixator is used to distract the lateral column, acting against pins placed in the cuboid and calcaneous bones. Correction of the medial longitudinal arch and the heel valgus to neutral or slight valgus serve as endpoints for the distraction. The forefoot is also rotated into neutral position prior to graft insertion.

The graft material is typically obtained from the iliac crest and then fashioned to fit into the distracted calcaneocuboid joint. In this procedure, the bone graft is typically wider both dorsally and laterally and tapering towards the plantar and medial aspects, respectively. A cervical plate placed laterally with two screws in the calcaneous and two screws in the cuboid complete the fusion. The remainder of the calcaneocuboid joint is then filled with cancellous graft.

One obvious drawback of this known fusion procedure is that it requires an additional surgery to remove the graft material from the iliac crest. Another drawback is that the graft material must be manually shaped to an appropriate shape and dimension during the surgical procedure, which is time-consuming and cumbersome. Finally, these known fusion techniques still require the use of a fixation plate to sufficiently immobilize the joint for arthrodesis to occur.

SUMMARY OF THE INVENTION

These and other drawback of prior fusion techniques are addressed by the present invention which provides a lengthening plate configured for engagement across the calcaneocuboid joint or across a space formed in the calcaneus bone. In one aspect of the invention, the plate includes an array of screw holes at its opposite ends, each arranged for solid fixation to the corresponding bone. The plate and screw holes may be configured for placement in either the right or left lateral column by rotating the plate to fit the foot anatomy.

In one feature of the invention, the plate includes a wedge projecting from the bone engaging surface of the plate. The wedge is sized depending upon the particular application (i.e., fusion of the calcaneocuboid joint or arthrodesis of a space formed in the calcaneus) and upon the patient's anatomy. The wedge is preferably tapered towards the plantar aspect with the greater width at the plate bone engaging surface. In addition, the wedge is preferably tapered toward the medial aspect so that the wedge includes a laterally facing end wall that is wider than the opposite medially facing end wall. In another aspect, the bone engaging surface of the plate is curved to more closely approximate the surface of the corresponding bones. In order to reduce the prominence of the plate, it has a minimum thickness. The wedge preferably has a height sufficient to span the calcaneus bone, whether disposed within the calcaneocuboid joint or within the calcaneus itself.

One benefit of the lengthening plate of the present invention is that it eliminates the need to extract cortical bone from elsewhere in the patient to fashion into a fusion wedge. Another benefit is that the inventive plate is configured for use in either known surgical lengthening technique—i.e., through widening the calcaneocuboid joint or lengthening the calcaneus bone. Other benefits and certain advantages of the present invention will become apparent upon consideration of the following written description taken together with the accompanying figures.

DESCRIPTION OF THE PREFERRED EMBODIMENTS

Figure 1:
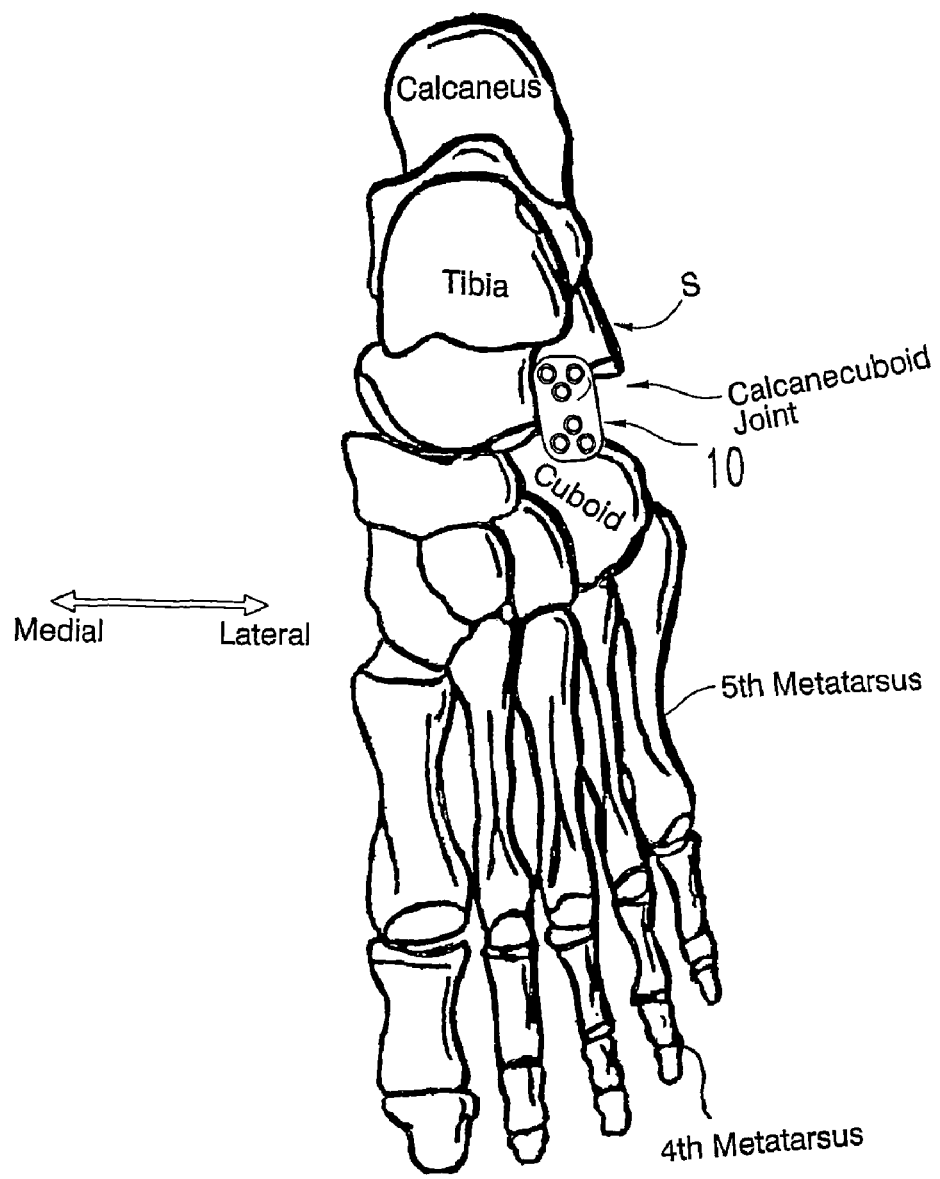
FIG. 1 is an enlarged view of dorsal aspect of the calcaneocuboid joint with a lengthening plate according to the present invention positioned over the joint.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIG. 1, a view of the dorsal aspect of the lateral column of the left foot is shown. In particular the cuboid bone, the distal portion of the calcaneus bone and the proximal portion of the fourth and fifth metatarsal bones are shown. The present invention contemplates a lengthening plate 10 that is configured for introduction within the calcaneocuboid joint or within an opening prepared in the calcaneus itself. It is understood that either the joint or calcaneus bone may be prepared in accordance with known surgical techniques to accept the plate 10 for the purposes of lengthening the lateral column of the foot. In preparing the calcaneus for lengthening, one typical procedure includes forming a space at a location S proximal to the calcaneocuboid joint as indicated in FIG. 1. This lengthening is especially beneficial for correcting flatfoot or hyperpronation.

Figure 2:
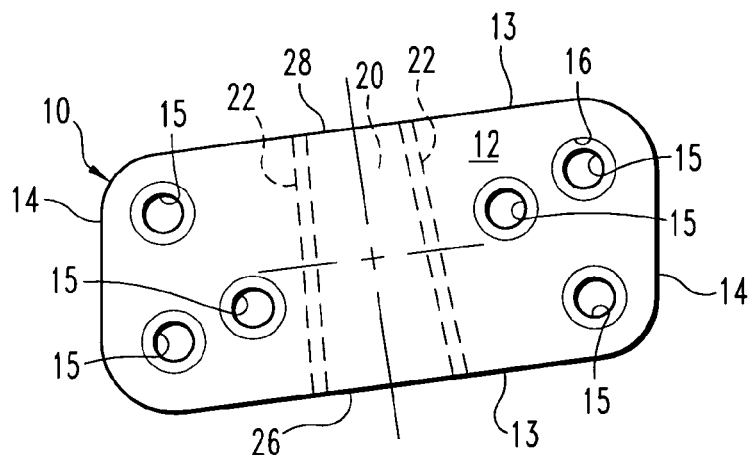
FIG. 2 is a top elevational view of the plate shown in FIG. 1.
Figure 3:
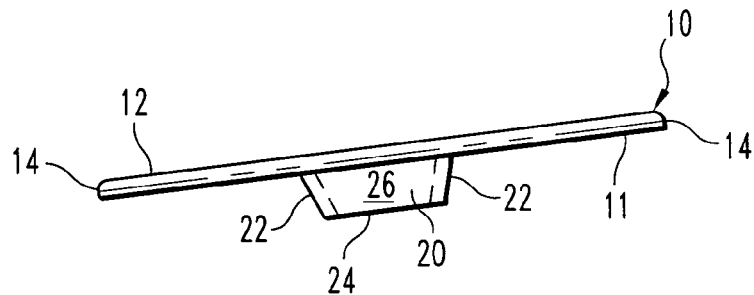
FIG. 3 is a side elevational view of the plate shown in FIG. 2.
Figure 4:
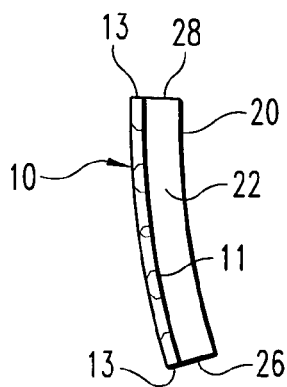
FIG. 4 is an end elevational view of the plate shown in FIG. 2.
Figure 5:
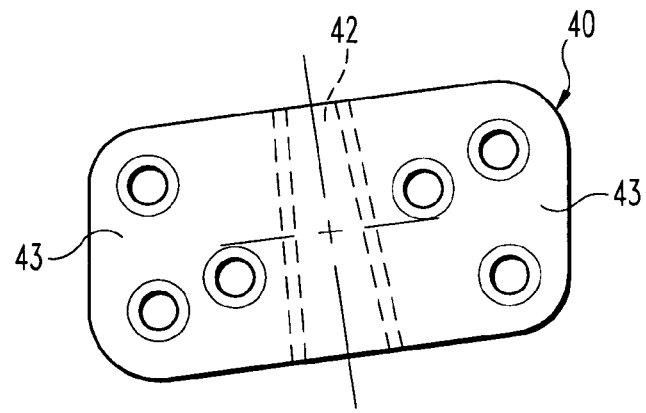
FIG. 5 is a top elevational view of a smaller plate for use in lieu of the plate shown in FIGS. 1-4.

The details of the plate 10 are more specifically shown in FIGS. 2-4. In particular, the plate 10 includes a bone engaging surface 11 that is preferably curved as shown in FIG. 3 to generally conform to the surface of either the calcaneus or the cuboid bones. In one specific embodiment, the surface 11 is curved across the width of the plate at a radius of about 43 mm which allows the plate 10 to lie as flush as possible with the surface of the subject bones of the foot. Most preferably, the entire plate from surface 11 to its upper surface 12 is formed at that radius. In order to further reduce the prominence of the plate above the bones, the plate has a minimal thickness between the two surfaces 11, 12. In a specific embodiment, the plate has a thickness of about 1.0 mm.

As seen in FIG. 2, the plate 10 is preferably in the form of a parallelogram in which the side edges 13 are non-perpendicular with the end edges 14. This form allows for optimal positioning of screw holes 15 at the opposite ends of the plate. This positioning of the screw holes enhances the engagement of the plate to each of the bones or bone segments spanning the gap to be widened, and ensures that bone screws passing through the holes 15 do not conflict or contact within the bone. In a most preferred embodiment, the screw holes include a circumferential chamfer, which facilitates the use of differently sized bone screws. For instance, in a specific embodiment of the invention, the screw holes 15 and chamfers 16 are configured to accept either 2.7 mm or 3.5 mm screws. The present invention contemplates that any combination of screw sizes may be used to fasten the ends of the plate 10 to the respective bone or bone segment. This aspect of the invention may be particularly useful where certain deficiencies exist in the subject bone.

The screws may be locking or non-locking type screws. In the case of locking screws, the screw holes 15 can be threaded (not shown) as is known in the art. In one specific embodiment, the screw holes may include 0.5 mm pitch threads cut at a 12° taper with a 3.6 mm minor diameter and a 4.0 mm major diameter.

It can be appreciated that the parallelogram configuration of the plate 10 allows the plate to be used on either the right or left foot (the left foot is depicted in FIG. 1). Thus, a single plate may be used universally by simply rotating the plate from one orientation to another. The pattern of the screw holes 15 places the greater number of screws at the farthest distance from the space to be expanded by the plate 10. In the most preferred embodiment, a triangular pattern of screw is implemented, as shown in FIG. 1.

In an important aspect of the invention, the plate 10 includes a wedge element 20 projecting from the bone engaging surface 11. The wedge is most preferably integral with the surface 11. However, it is contemplated that the wedge may be separately fastened to the plate when the plate is constructed, such as by welding. As a further alternative, the plate and wedge may incorporate a mechanical engagement feature, such as a tongue and groove arrangement, to allow the wedge element 20 to be engaged to the plate at any time.

The wedge element 20 is tapered in two degrees of freedom. In one degree of freedom, the side walls 22 are tapered medially, as best seen in FIG. 2. The side walls 22 are tapered from a wider laterally facing end wall 26 to a narrower medially facing end wall 28. This configuration of the wedge element 20 will produce a wider distracted space at the lateral aspect of the lateral column versus the width of the space at the medial aspect. With the plate positioned medially, as shown in FIG. 1, sufficient distracted space is provided at the lateral aspect for the introduction of cancellous bone or other osteogenic material into the space to assist in osteoinduction and complete fusion. In a specific embodiment of the invention, at the bottom wall 24 the laterally facing end wall 26 has a width of about 8.0 mm and the medially facing end wall 28 has a width of about 6.0 mm.

The wedge element 20 is also tapered toward the plantar aspect of the foot. This, the side walls 22 taper from the surface 11 to a narrower bottom wall 24, as best seen in FIG. 3. In one specific embodiment, the wedge element 20 has a width of about 10.0 mm tapering to 8.0 mm at the surface 11, while the bottom wall has a width of about 8.0 mm tapering to about 6.0 mm. This dorsal-to-plantar tapering accommodates the change in the foot arch as the lateral column is lengthened to achieve a more appropriate arch.

In an alternative embodiment, a smaller plate 40 may be provided that incorporates a smaller wedge element 42. In this embodiment, the mounting portions 43 accommodate the same screw hole dimensions and patterns as in the larger plate 10. In this embodiment, only the wedge element 42 is smaller in width. The present invention contemplates lengthening plates having various wedge element widths, such as ranging from 6.0 mm to 12.0 mm. This array of fixed widths can accommodate the lateral column lengthening needs of a wide range of patients and procedures.

In the illustrated embodiments, the wedge elements 20, 42 extend across the entire width of the corresponding plate 10, 40. Alternatively, the wedge elements may extend only partially across the width, and may be centrally positioned or skewed to one side (preferably medially). This modification to the wedge element creates more space for the introduction of bone graft or other osteogenic material into the distracted space. As a further alternative, the wedge element may be at least partially hollow to accept bone osteoconductive or osteoinductive material, with the focus on decreasing time to fusion or complete osteogenesis of the distracted space. With this alternative, the wedge element may include bone ingrowth openings defined in the side walls 22. It is important, however, that the structural integrity of the wedge element be maintained so that the wedge element can maintain the distraction under ligament pressure.

The lengthening plate 10, 40 is formed of a biocompatible material, most preferably a metal such as titanium. In one specific embodiment, the metal is titanium alloy TI-6AL-4V. Other materials are contemplated provided the strength of the resulting plate is not compromised for the intended application of lengthening the lateral column of the foot. The wedge element may be formed of a resorbable material that becomes part of the fusion mass, rather than integrated into the fusion mass.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method of lengthening a lateral column of a foot having a cuboid and a calcaneus, comprising:
   (a) creating a calcaneocuboid space in the lateral column of the foot between the cuboid and the calcaneus;
   (b) positioning a metallic plate assembly into contact with the cuboid and the calcaneus, the metallic plate assembly including a plate portion and wedge element that are monolithically formed together, wherein:
      the metallic plate assembly is configured so that the wedge element projects from a bone engaging surface of the plate portion,
      the wedge element includes (i) a laterally facing end wall that projects from said bone engaging surface, and (ii) a medially facing end wall that projects from said bone engaging surface,
      the wedge element (i) tapers inwardly from the bone engaging surface to an opposite bottom wall of said wedge element, and (ii) tapers inwardly from the laterally facing end wall to the medially facing end wall, and
      the positioning step includes (i) locating the wedge element in the calcaneocuboid space, and (ii) placing the bone engaging surface of the plate portion against both the cuboid and the calcaneus; and
   (c) fastening the plate portion to both the cuboid and the calcaneus with screws.

2. The method of claim 1, further comprising placing a bone graft in the calcaneocuboid space.

3. The method of claim 1, wherein the metallic plate assembly is formed from titanium.

4. The method of claim 1, wherein said wedge element tapers uniformly from said bone engaging surface to said opposite bottom wall of said wedge element.

5. The method of claim 1, wherein:
   said plate portion has a length and a width, and
   said plate portion is curved along the width thereof.

6. The method of claim 1, further comprising placing a bone ingrowth material in the calcaneocuboid space adjacent to the wedge element.

7. The method of claim 1, wherein locating the wedge element in the calcaneocuboid space includes:
   positioning (i) a lateral portion of the cuboid a first distance away from a lateral portion of the calcaneus, and (ii) a medial portion of the cuboid a second distance away from a medial portion of the calcaneus, and
   said first distance is greater than said second distance.

8. The method of claim 1, wherein the step (c) comprises:
   (c1) fastening an anterior part of the plate portion to a superior portion of the cuboid; and
   (c2) fastening a posterior part of the plate portion to a superior portion of the calcaneus.

9. The method of claim 8, wherein the step (c1) comprises:
   selecting at least one hole from a set of three holes through the anterior part of the plate portion; and
   inserting a bone screw through the selected at least one hole.

10. The method of claim 9, further comprising:
    locking the bone screw to the anterior part of the plate portion.

* * * * *

UNITED STATES PATENT AND TRADEMARK OFFICE
CERTIFICATE OF CORRECTION

| | | |
|---|---|---|
| PATENT NO. | : 7,931,680 B2 | Page 1 of 1 |
| APPLICATION NO. | : 11/094993 | |
| DATED | : April 26, 2011 | |
| INVENTOR(S) | : Mark Myerson et al. | |

It is certified that error appears in the above-identified patent and that said Letters Patent is hereby corrected as shown below:

<u>Column 2,</u>
Line 27, replace "drawback" with --drawbacks--

<u>Column 4,</u>
Line 43, replace "This," with --Thus,--

Signed and Sealed this
Fifth Day of March, 2013

Teresa Stanek Rea
*Acting Director of the United States Patent and Trademark Office*